United States Patent [19]

Fuseya et al.

[11] 4,246,333
[45] Jan. 20, 1981

[54] DEVELOPMENT INHIBITOR PRECURSOR AND A PHOTOGRAPHIC ELEMENT CONTAINING THE SAME

[75] Inventors: Yoshiharu Fuseya; Yukio Karino; Yoshio Sakakibara; Katsusuke Endo, all of Minami-ashigara, Japan

[73] Assignee: Fuji Photo Film Co., Ltd., Minami-ashigara, Japan

[21] Appl. No.: 26,506

[22] Filed: Apr. 3, 1979

[30] Foreign Application Priority Data

Apr. 3, 1978 [JP] Japan .................................. 53/38931

[51] Int. Cl.$^3$ .......................... G03C 1/40; G03C 1/10; G03C 5/30
[52] U.S. Cl. .................................... 430/219; 430/544; 430/559; 430/564; 430/957
[58] Field of Search ................... 96/66.3, 77, 76 R, 95, 96/29 D, 109; 430/219, 544, 957, 559, 564

[56] References Cited

U.S. PATENT DOCUMENTS

| | | |
|---|---|---|
| 3,260,597 | 7/1966 | Weyerts et al. ..................... 96/29 D |
| 3,839,041 | 10/1974 | Hiller ..................... 96/109 |
| 4,009,029 | 2/1977 | Hammond et al. ....................... 96/77 |

Primary Examiner—Richard L. Schilling

Attorney, Agent, or Firm—Sughrue, Rothwell, Mion, Zinn and Macpeak

[57] ABSTRACT

A photographic element having on a support at least one silver halide emulsion layer having associated therewith a development inhibitor precursor represented by the formula (I)

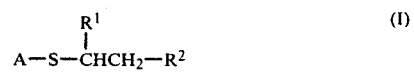

wherein A is a phenyl group, a substituted phenyl group or a 5- or 6-membered nitrogen-containing heterocyclic ring; said A splitting together with the sulfur atom in the above molecule from the residue of the molecule to provide a silver halide development inhibitor; $R^1$ is an alkyl group having 1 to 4 carbon atoms; and $R^2$ is a cyano group, a carbamoyl group or the group represented by the formula

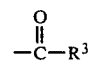

wherein $R^3$ is an aryl group.

16 Claims, No Drawings

DEVELOPMENT INHIBITOR PRECURSOR AND A PHOTOGRAPHIC ELEMENT CONTAINING THE SAME

BACKGROUND OF THE INVENTION

1. Field of the Invention

This invention relates to a photographic element and a novel development inhibitor precursor for photographic elements. More particularly, this invention relates to a photographic element for color diffusion transfer process using a novel development inhibitor precursor.

2. Description of the Prior Art

Development inhibitors and development inhibitor precursors for use in a photographic element for color diffusion transfer photographic process are known as disclosed in, for example, U.S. Pat. No. 3,260,597 to Weyers et al and U.S. Pat. No. 3,265,498 to Rogers. However, the compounds disclosed in these patents inhibit not only the occurrence of unnecessary development but also the occurrence of necessary development, which results in reducing the quality of images.

Also, photographic development is greatly influenced by temperature, i.e., development proceeds slowly at low temperatures but proceeds faster at higher temperatures and, in particular, development is liable to proceed excessively fast at high temperatures. Therefore, it has been desired to find development inhibitor precursors which enlarge the allowable range of processing temperatures by inhibiting the occurrence of unnecessary development and controlling the necessary development so that it is not implemented at about room temperature, and, in particular, inhibiting the occurrence of excessive development at high temperatures.

U.S. Pat. No. 4,009,029 to Hammond et al discloses some development inhibitor precursors for this purpose. The various photographic additives used in photographic elements must, on the one hand, exhibit their effect but, on the other hand, the additives or the reaction products of the additives must not give undesirable effects such as reduction in image quality before as well as after processing the photographic elements. The compounds described in U.S. Pat. No. 4,009,029, for example, 5-(2-cyanoethylthio)-1-phenyltetrazole form an injurious compound (by product) which promotes the destruction of certain image-forming dyes formed upon processing photosensitive elements. If the additive which forms such an injurious compound exists in a photographic element, the color image density is reduced and the image quality is degraded as time passes after processing. Therefore, it has further been desired to find the development inhibitor precursors which can properly control the occurrence of development, possess a wide allowable range for processing temperature, and reduce the quality of color images after processing less.

SUMMARY OF THE INVENTION

A first object of this invention is to provide novel development inhibitor precursors.

A second object of this invention is to provide a photographic element having coated on a support at least one silver halide emulsion layer associated with these novel development inhibitor precursors.

A third object of this invention is to provide a photographic element for color diffusion transfer process capable of giving color images of improved image quality, in particular, of low $D_{min}$.

A fourth object of this invention is to provide a photographic element for color diffusion transfer process having a wide allowable range of processing temperatures.

A fifth object of this invention is to provide a photographic element for color diffusion transfer process capable of giving color images having excellent stability, in particular, showing less fading, during storage thereof after processing.

A sixth object of this invention is to provide a photographic element for color diffusion transfer process using the novel development inhibitor precursor having improved properties.

It has been found that the above-described objects of this invention can be attained by the novel development inhibitor precursors represented by the following formula (I)

wherein A represents a phenyl group, a substituted phenyl group (a preferred substituent is one having a positive substituent constant $\sigma$, e.g., a —Cl atom, a —Br atom, a —$CONH_2$ group, a —CHO group, a —$COCH_3$ group, a —$COOC_2H_5$ group, a —CN group, a —$NO_2$ group, etc., and these substituents are described in "Advanced Organic Chemistry"; 2nd edition, page 253 by J. March), or a 5- or 6-membered nitrogen-containing heterocyclic ring including substituted rings or rings condensed with another ring (typical examples of the heterocyclic ring are a tetrazole ring, a 1,2,4-triazole ring, a benzooxazole ring, a benzothiazole ring, a pyridine ring, a pyrimidine ring, etc.); said A splitting together with the sulfur atom in the molecule to provide a silver halide development inhibitor; $R^1$ represents a straight or branched chain unsubstituted alkyl group of 1 to 4 carbon atoms; and $R^2$ represents a cyano group, a carbamoyl group (which may be substituted with an alkyl ($C_1$–$C_8$) group or an aryl ($C_6$–$C_{12}$) group such as a phenyl group), or the group of the formula

wherein $R_3$ represents an mono- or bi-cyclic aryl ($C_6$–$C_{12}$) group including a substituted aryl group, preferably a phenyl group or a substituted phenyl group and examples of the substituent are an alkyl group of 1 to 4 carbon atoms, an acylamino ($C_1$–$C_{16}$) group (e.g., acetylamino group) or an alkoxy ($C_1$–$C_{18}$) group (e.g., octyloxy group, octadecyloxy group, etc.).

That is, according to one embodiment of this invention, there is provided the novel development inhibitor for precursors represented by formula (I).

According to another embodiment of this invention, there is provided a photographic element, in particular, a photographic element for color diffusion transfer process containing the novel development inhibitor precursors shown in formula (I).

DETAILED DESCRIPTION OF THE INVENTION

The compounds of general formula (I) wherein $R_2$ is a cyano group and A is a 5- or 6-membered nitrogen-containing heterocyclic ring are particularly preferred and represented by the following formula (II)

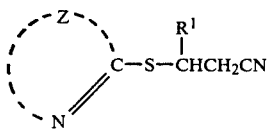

wherein Z represents a non-metallic atomic group necessary to complete a 5- or 6-membered heterocyclic ring including other hetero atom(s) (such as, N, O, S) and a substituted ring (examples of the substituents are an alkyl ($C_1$–$C_{14}$, preferably $C_1$–$C_{10}$) group such as a methyl group, etc., an aryl ($C_6$–$C_{12}$, preferably $C_6$–$C_{10}$) group such as a phenyl group, etc., an aralkyl ($C_3$–$C_{12}$, preferably $C_3$–$C_{10}$) group such as a benzyl group, etc.), an alkylthio ($C_1$–$C_{10}$) group, arylthio ($C_6$–$C_{10}$) group, an alkylamino ($C_1$–$C_{10}$) group, an arylamino ($C_6$–$C_{10}$) group, an acylamino ($C_1$–$C_{10}$) group and an alkoxy ($C_1$–$C_{10}$) group and a condensed aromatic ring such as a benzene ring; said heterocyclic ring splitting together with the sulfur atom of the molecule from the residue of the molecule to provide a silver halide development inhibitor and $R^1$ represents an alkyl group of 1 to 4 carbon atoms (e.g., a methyl group, an ethyl group, a propyl group, a t-butyl group, etc.).

In another very preferred embodiment of the development inhibitor precursors in this invention, Z is an atomic group necessary for completing a tetrazole ring preferably a phenyltetrazole ring and $R^1$ is a methyl group in general formula (II).

The development inhibitor precursor useful in this invention generally splits in an alkaline solution to release a development inhibitor which can diffuse in an alkaline solution.

Typical examples of the development inhibitor precursors useful in this invention are illustrated below:

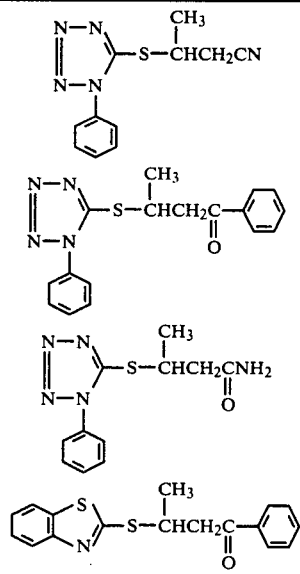

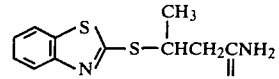
Compound 5

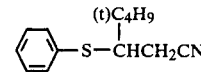
Compound 6

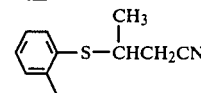
Compound 7

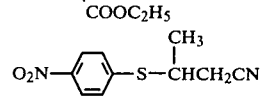
Compound 8

The development inhibitor precursor of this invention is prepared by Michael Reaction by adding an olefine (1.1 to 4.0 equivalent) to a development inhibitor (1.0 equivalent) in the presence of a basic catalyst.

Examples for preparing these compounds are shown below.

SYNTHESIS EXAMPLE 1

Preparation of Compound 1

To 3.56 g (0.02 mol) of 1-phenyl-5-mercaptotetrazole are added 9 ml of acetic acid, 1 ml of methanol, 1.64 g of potassium acetate (as a catalyst) and 2.68 g (0.04 mol) of crotononitrile and the mixture is refluxed for 16 hours at 105° C. After the reaction is over, 50 ml of water is added to the reaction mixture, whereby an oily material is separated. After allowing to stand overnight, the oily material is crystallized and by recrystallizing the crystals formed from methanol, 2.6 g of Compound 1 having a melting point of 84°–85° C. is obtained (yield: 53%).

| Elemental analysis for $C_{11}H_{11}N_5S$: | | | |
|---|---|---|---|
| C | H | N | S |
| Calculated: 53.87% | 4.52% | 28.56% | 13.07% |
| Found: 53.73% | 4.40% | 28.67% | 13.17% |

SYNTHESIS EXAMPLE 2

Preparation of Compound 8

To 3.1 g (0.02 mol) of p-nitrothiophenol are added 15 ml of ethanol, 1.6 g of sodium acetate (as a catalyst), and 1.5 g (0.022 mol) of crotononitrile and the mixture is refluxed for 4 hours. After the reaction is over, the reaction mixture is cooled. Insoluble matters are filtered off and the filtrate is concentrated under reduced pressure and applied to a column chromatography to provide Compound 8 as a yellow liquid.

| Elemental analysis for $C_{10}H_{10}N_2O_2S$: | | | |
|---|---|---|---|
| C | H | N | S |
| Calculated: 54.05% | 4.54% | 12.61% | 14.43% |
| Found: 53.76% | 4.44% | 12.59% | 14.52% |

Other development inhibitor precursors of this invention may be prepared by the methods known in the art as described in, for example, C. F. H. Allen and W. J. Humphlett; *Canadian Journal of Chemistry*; Vol. 44, pages 2315–2321 (1966) and R. M. Ross; *Journal of*

*American Chemical Society*, Vol. 71, pages 3458–3459 (1949).

The compounds of this invention have the feature that they give very low degradation effect to dye images, that is they can provide color prints which can be stored stably for a long period of time as compared with the compounds described in above-mentioned U.S. Pat. No. 4,009,029. Such a large profitability of the compounds of this invention is generally an unexpected and novel result because they are similar to known compounds in chemical structure (the hydrogen atom is substituted by a lower alkyl group). It is believed that the profitability of the compounds of this invention is based at least partially in that the reaction products released upon splitting of the compounds of this invention by alkali processing have very low reactivity with the dyes forming color images as compared with those of the known compounds.

The release of a developing inhibitor from the development inhibitor precursor of this invention is generally attained by contact with an alkaline medium but can be also attained or promoted by increasing temperatures. Desired releasing speeds of the development inhibitor from the development inhibitor precursor are different due to the system used. The splitting reaction of the development inhibitor precursor by alkali is a first-order reaction and, therefore, the higher the pH the faster the splitting reaction speed. The pH of the color diffusion transfer processing solution is preferably 12 or more.

The development inhibitor precursors of this invention can be profitably applied to the above-mentioned photographic elements for diffusion transfer process as well as conventional photosensitive materials containing silver halide emulsions. The compounds of this invention are stable when they are incorporated into the photosensitive materials, do not or substantially do not injure the photographic properties during the preservation of the photosensitive materials, do not reduce the photosensitivity of the photosensitive materials upon light-exposure, and can release mercapto compounds during development acting as anti-fogging agent to effectively reduce the formation of fog. The compounds of this invention can inhibit the formation of fog in a rapid development process using silver halide emulsions of high development speed, silver halide emulsions associated with development accelerators or couplers having high reactivity, developers having high pH, or in the case of employing high development temperatures. The precursors of this invention are inactive toward silver halide emulsions as precursors and scarcely split even in severe preserving conditions with which photosensitive materials meet.

The excellent stability of the precursors of this invention associated with silver halide emulsions cannot be obtained with conventional precursors for mercapto-type develoment inhibitors, for example, the sparingly soluble metal salts of mercapto compounds described in U.S. Pat. No. 3,649,267 and the acyl derivatives of mercapto compounds described in U.S. Pat. No. 3,311,474, Japanese Patent Application (OPI) No. 8,826/'77 and French Pat. No. 1,586,036.

In case of incorporating the compounds of this invention in silver halide emulsion layers or layers adjacent to silver halide emulsion layers, it is profitable to use the compounds in an amount of from about $10^{-4}$ mol to about $5 \times 10^{-2}$ mols per mol of the silver halide in the silver halide emulsion layer.

In general, a so-called diffusion transfer photographic process is known wherein a photosensitive element having silver halide emulsion layers is imagewise exposed and developed to form imagewise distributed diffusible image-forming materials as the result of the development of exposed silver halide grains and diffusible dye image-forming materials are transferred by diffusion into other hydrophilic colloid layers and fixed therein, and photographic elements of various types and for various systems have been proposed.

Typical examples of them are described in, for example, U.S. Pat. Nos. 2,983,606; 3,415,644; 3,415,645; 3,415,646; and 3,647,437; Canadian Pat. Nos. 674,082 and 682,157; and Belgian Pat. Nos. 757,959; 757,960; etc. For example, there are a so-called peel-apart systems in which a dye image-receiving layer and photosensitive silver halide emulsion layers are formed on different supports and after exposure and processing, the dye image-receiving element is peeled apart for observation of dye images; a system in which a dye image-receiving layer and photosensitive silver halide emulsion layers are formed on different supports and after exposure and processing, dye images transferred to the dye image-receiving layer are observed with white background through a transparent support without peeling the dye image-receiving element; and also a system using a so-called laminated negative image-receiving element comprising a dye image-receiving layer, a white reflective layer, a light shielding layer, and photosensitive silver halide emulsion layers on the same support. The development inhibitor precursors of this invention are used in any of these systems with remarkable effects.

A preferred embodiment of this invention is a photographic element having on a support at least one silver halide emulsion layer associated with the development inhibitor precursor of this invention shown by formula (I) in such manner that the precursor can effectively inhibit development.

Also, a very preferred embodiment of this invention is a photosensitive element including (i) photosensitive layers including at least one silver halide emulsion layer associated with a dye image-providing material, (ii) an image-receiving layer, (iii) a mechanism for releasing an alkaline processing composition containing a silver halide developing agent, (iv) a neutralizing mechanism including a neutralizing layer associated, if necessary, with a neutralization timing layer, and (v) the development inhibitor precursor of this invention incorporated in the photographic element in such a manner that the precursor effectively inhibits development of the above-mentioned silver halide emulsion.

The development inhibitor is adsorbed on silver halide grains and, thereby, the development inhibitor disturbs, inhibits or delays a reaction between the silver halide and the developing agent. In a preferred embodiment, after the processing solution is processed, desirable development of the silver halide occurs and the development inhibitor is released and diffused and inhibits undesirable development (such as, increase of $D_{min}$).

The development inhibitor precursor shown by formula (I) may be incorporated in any layer or layers of a photographic material if the precursor is so associated that it acts effectively to inhibit the development of silver halide emulsion, but the precursor is preferably incorporated in a photosensitive layer such as a layer containing a silver halide emulsion, a layer containing a dye image-providing material, and other auxiliary layers such as an image-receiving layer and a white reflective layer, or in the neutralizing mechanism such as in a neutralizing layer or in a neutralization timing layer. It is particularly preferred that the precursor is incorporated in a neutralizing layer or a neutralization timing layer.

The amount of the above-mentioned development inhibitor precursor used in a diffusion transfer photographic process depends upon the development conditions and the formulation of the layer containing the silver halide emulsion but is at least about $10^{-5}$ mol, preferably from about $10^{-4}$ to $10^{-1}$ mol per mol of silver.

The development inhibitor precursor can be dispersed in a desired layer by technically any conventional and effective method. In a preferred embodiment, the development inhibitor precursor is first dissolved in a high boiling solvent such as a water-insoluble color former solvent (such as, tricresyl phosphate, dibutyl phthalate) and then dispersed as the solution in a carrier material. Typical and useful examples of the color former solvent are the liquid dye stabilizers described in "Improved Photographic Dye Image Stabilizer-Solvent" in *Product Licensing Index;* Vol. 83 published on March 1971 and suitable polar solvents such as tri-o-cresyl phosphate, di-n-butyl phthalate, diethyl lauryl amide, 2,4-diallyl phenol, etc. In another preferred embodiment, the development inhibitor precursor is loaded to a polymer latex as described, for example, Japanese Patent Application (OPI) Nos. 59,942/'76 (which corresponds to U.S. Patent Application Ser. No. 506,912 filed on Sept. 17, 1974 and U.S. Patent Application Ser. No. 575,570 filed on May 8, 1975 and also corresponding to W. German Patent Application (OLS) No. 2,541,230) and 59,943/'76 (which corresponds to U.S. Patent Application Ser. No. 506,919 filed on Sept. 17, 1974 and U.S. Patent Application Ser. No. 575,689 filed on May 8, 1975 and also corresponding to W. German Patent Application (OLS) No. 2,541,274). In a further preferred embodiment, the development inhibitor precursor is directly dissolved in a coating composition in case of forming a neutralizing layer or a neutralization timing layer using an organic solvent. The precursor of this invention may be added by any other methods than those above.

The silver halide emulsion used in this invention in such a manner as associated with the development inhibitor precursor is a hydrophilic colloid-like dispersion of silver chloride, silver bromide, silver chlorobromide, silver iodobromide, silver chloroiodobromide or a mixture of them and the halogen composition is selected according to the purpose and processing condition of the photosensitive materials but it is preferred that the content of iodide be 10 mol percent or less. The grain size of the silver halide used may be an ordinary grain size or fine grain size but the silver halide having a mean grain size of from about 0.1 micron to about 2 microns is preferably used. Furthermore, according to the purpose of the photosensitive materials, silver halide grains having uniform grain size are desirable. The crystal form of the silver halide grains used may be a cubic system, an octahedron, or a mixed crystal. These silver halide emulsions may be prepared by conventional methods as described in, for example, P. Glafkides, *Chimie Photographique,* 2nd edition, Chapter 18 to Chapter 23, published in 1957 by Paul Montel, Paris.

It is desirable that the silver halide emulsion used in this invention be chemically sensitized using a natural sensitizer contained in gelatin; a sulfur sensitizer such as sodium thiosulfate, N,N,N'-triethylthiourea, etc.; a gold sensitizer such as thiocyanate complex salt and thiosulfate complex salt of mono-valent gold; or a reductive sensitizer such as stannous chloride, hexamethylenetetramine, etc.

In this invention, an ordinary negative type silver halide emulsion which is liable to form latent images on the surface of silver halide grains as well as a so-called direct reversal silver halide emulsion (e.g., an internal latent image type silver halide emulsion or a solarization type silver halide emulsion) which is developed at unexposed areas may be used. The solarization type silver halide emulsion described in Mees, *The Theory of the Photographic Process,* pages 261 to 297, published in 1942 by McMillan Co., New York is profitably used. The process of the preparation of such a silver halide emulsion is described in, for example, U.K. Pat. Nos. 443,245 and 462,730; U.S. Pat. Nos. 2,005,837, 2,541,472; 3,367,778; 3,501,305; 3,501,306; and 3,501,307. Also, the internal latent image type direct positive silver halide emulsion is described in U.S. Pat. Nos. 2,497,875; 2,588,982; 2,456,953; 3,761,276; 3,206,313; 3,317,322; 3,761,266; 3,850,637; 3,923,513; 3,736,140; 3,761,267; and 3,854,949.

In the case of using the direct reversal photographic emulsion, direct positive images can be obtained by developing the photographic emulsion, after image exposure, in the presence of a fogging agent or by fogging the photographic emulsion by uniformly exposing, after image exposure, the photographic emulsion (a high illumination exposure for a short period of time, i.e., an exposure for a time shorter than $10^{-2}$ sec. or a low illumination exposure for a long period of time) during the surface developing process. However, the use of a fogging agent is preferred in the point that the fogging extent can be easily controlled. The fogging agent may be incorporated in photosensitive materials or a developer but the former system is preferred. As the fogging agent of this type, there are, for example, the hydrazines described in U.S. Pat. Nos. 2,588,982 and 2,568,785; hydrazide and hydrazone described in U.S. Pat. No. 3,227,552; the quaternary salt compounds described in U.S. Pat. No. 1,283,835; Japanese Patent Publication No. 38,164/'74 and U.S. Pat. Nos. 3,734,738; 3,719,494 and 3,615,615; and the acylhydrazinophenylthiourea series compounds described in German Pat. No. 2,635,316.

The amount of the fogging agent used in this case may be changed in a wide range depending on the result desired. When the fogging agent is incorporated in photosensitive materials, the concentration of the fogging agent depends on the kind of the fogging agent used but is usually about 0.1 mg to about 1500 mg, preferably 0.5 mg to 700 mg per mol of silver. When the fogging agent is incorporated in a developer, the amount thereof is generally from about 0.05 to about 5 g, preferably from 0.1 g to 1 g, per liter of the developer. When the fogging agent is incorporated in a photographic layer of a photosensitive material, it is effective, as the case may be, to render the fogging agent non-diffusible. As the means for rendering the fogging agent non-diffusible, it is effective to bond a ballast group usually used for photographic couplers to the fogging agent.

The silver halide emulsion used in this invention can be stabilized by a conventional stabilizer. Furthermore, the silver halide emulsion used in this invention may contain a sensitizing compound such as a polyethylene oxide compound.

The silver halide emulsion used in this invention may be, if desired, spectrally sensitized. As the useful spectral sensitizers, there are cyanines, merocyanines, holopolarcyanines, styryls, hemicyanines, oxanoles, hemioxanoles, etc. Practical examples of the spectral sensitizers used in this invention are described in, for example, P. Glafkides, *Chimie Photographique*, 2nd edition, Chapters 35–41 and F. M. Hamer, *The Cyanine and Related Compounds,* Interscience. In particular, the cyanines each substituted at the nitrogen atom of the basic heterocyclic ring nucleus by an aliphatic group (e.g., alkyl group) having hydroxyl group, carboxy group, or sulfo group as described in, for example, U.S. Pat. Nos. 2,503,776; 3,459,553 and 3,177,210 are useful in the practice of this invention.

As the dye image-providing materials for diffusion transfer process used in the manner associated with the photographic silver halide emulsions in this invention, there are the dye developing agents and various compounds described in, for example, U.S. Pat. Nos. 2,983,606; 3,230,085; 3,227,551; 3,227,554; 3,443,939; 3,443,940; 3,551,406; 3,658,524; 3,698,897; 3,725,062; 3,728,113; 3,751,406; 3,928,312; 3,929,760; 3,931,144; 3,932,380; 3,932,381; 3,942,987; 3,993,638; 4,055,428; 4,076,529; U.K. Pat. Nos. 840,731; 904,364; 1,038,331; German Offenlegungsschriften (OLS) Nos. 1,930,215; 2,214,381; 2,228,361; 2,242,762; 2,317,134; 2,402,900; 2,406,626; 2,406,653; 2,406,664; Japanese Patent Application (OPI) Nos. 104,343/'76 (corresponding to W. German Patent Application (OLS) No. 2,505,248) and 63,324/'77 and Research Disclosure 166 No. 16629 (Feb., 1978). In particular, the use of the dye image-providing material of the type that the material is originally non-diffusible but splits after the oxidation reduction reaction with the oxidized product of a developing agent to release a diffusible dye (hereinafter, this material is referred to as a DRR compound) is preferred.

Practical examples of the DRR compound are, in addition to the dye image-providing materials described in the above-mentioned patent specifications, such magenta dye-providing materials as 1-hydroxy-2-tetramethylene-sulfamoyl-4-[3'-methyl-4'-(2''-hydroxy-4''-methyl-5''-hexadecyloxyphenylsulfamoyl)phenylazo]-naphthalene, such yellow dye image-providing materials as 1-phenyl-3-cyano-4-{3'-[2''-hydroxy-4''-methyl-5''-(2''',4'''-di-t-phenylphenoxyacetamino)-phenylsulfamoyl]phenylazo}-5-pyrazolone, etc.

In the case of using the DRR compounds in this invention, any silver halide developing agent which can cross-oxidize the DRR compounds can be used. Such a developing agent may be incorporated in an alkaline processing composition (processing element) or in a proper layer of photosensitive element. Examples of the developing agent used in this invention are hydroquinone, an aminophenol such as N-methylaminophenol, etc., 1-phenyl-3-pyrazolidone, 1-phenyl-4,4-dimethyl-3-pyrazolidone, 1-phenyl-4-methyl-4-oxymethyl-3-pyrazolidone, N,N-diethyl-p-phenylenediamine, 3-methyl-N,N-diethyl-p-phenylenediamine, 3-methoxy-N-ethoxy-p-phenylenediamine, etc.

In the developing agents illustrated above, a black and white developing agent equipped with the property of reducing the formation of stain on an image-receiving layer (a mordanting layer) is particularly preferred.

When the DRR compound is used in the practice of this invention, a negative image is formed in the image-receiving portion as the transferred image and a positive image is formed in the photosensitive element in the case of using a so-called ordinary silver halide emulsion which is developed according to the amount of exposure. On the other hand, when the above-mentioned direct reversal silver halide emulsion in which the silver halide emulsion is developed at the unexposed areas is used, a positive image is obtained in the image-receiving portion of a film unit.

Moreover, with the DIR reversal emulsion system as described in U.S. Pat. Nos. 3,227,551; 3,227,554; and 3,364,022 or with the reversal emulsion system in dissolution physical development as described in U.K. Pat. No. 904,364, a transferred positive image can be obtained. In U.S. Pat. Nos. 3,227,550 and 3,227,552 and U.K. Pat. No. 1,330,524, there are described a series of processes for obtaining diffusion transfer color images.

Typical examples of the color developing agent in the case of using diffusible dye releasing couplers in this invention are the para-phenylenediamine derivatives described in U.S. Pat. Nos. 3,227,552; 2,559,643; and 3,813,244. Furthermore, the p-aminophenol derivatives as described in Japanese Pat. Application (OPI) No. 26,134/'73 can be advantageously used. It is preferred that such a color developing agent be in the alkaline processing composition contained in a rupturable container. Also, the color developing agent may be incorporated in a layer additionally formed at the negative portion of a film unit as well as may be incorporated in a silver halide emulsion layer of the film unit.

The photosensitive sheet used in this invention includes a support which does not undergo substantial dimensional deformation during processing. Examples of such a support are cellulose acetate films, polystyrene films, polyethylene terephthalate films, polycarbonate films, etc., used for conventional photographic materials. Other effective supports are paper or paper the surface of which is laminated with a polymer having water-impermeability, such as polyethylene.

The processing composition used in this invention is a liquid composition containing the processing components necessary for the development of silver halide emulsions and the formation of diffusion transfer dye images. The main solvent of the liquid processing composition is water and it may contain a hydrophilic solvent such as methanol, methyl cellosolve, etc. The processing composition further contains an alkali in an amount sufficient for maintaining the pH necessary for causing the development of silver halide emulsion layers and neutralizing an acid (e.g., a hydrohalogenic acid such as hydrobromic acid, etc., and a carboxylic acid such as acetic acid, etc.) formed during various steps of development and formation of dye images. Examples of the alkali are alkali metal salts, alkaline earth metal salts, and amines such as lithium hydroxide, sodium hydroxide, potassium hydroxide, a dispersion of calcium hydroxide, tetramethylammonium hydroxide, sodium carbonate, tri-sodium phosphate, diethylamine, etc., and it is preferred to use an alkali hydroxide in such a concentration that the pH of the processing composition is about 10 or more, particularly 12 or more at room temperature.

It is more preferred that the processing composition contains a hydrophilic polymer such as high molecular weight polyvinyl alcohol, hydroxyethyl cellulose, sodium carboxymethyl cellulose, etc. Such a polymer not only gives viscosity of 1 poise or more, preferably about 500 to 1,000 poises at room temperature to the processing composition and facilitates the uniform spreading of the composition at processing but also forms a nonflowable film when the processing composition is concentrated by the transfer of the aqueous solvent into the photosensitive element and the image-receiving element in the step of processing to help the film unit becoming unity after processing. The polymer film can contribute to prevent, after the formation of the diffusion transfer dye images is substantially finished, the dye images formed from being changed by inhibiting the further transfer of coloring components into the image-receiving layer.

The processing composition contains further, as the case may be, a light absorbing material such as titanium oxide, carbon black, and pH indicators as well as the desensitizers as described in U.S. Pat. No. 3,579,333 for preventing the silver halide emulsion layers from being fogged upon being exposed to external light during processing. Furthermore, the processing composition may additionally contain other development inhibitors such as a benzotriazole.

It is preferred that the above-mentioned processing composition is used in the rupturable container as described in U.S. Pat. Nos. 2,543,181; 2,643,886; 2,653,732; 2,723,051; 3,056,491; 3,056,492; and 3,152,515.

As the mordants used for the image-receiving layers for fixing the diffusible dyes formed from the above-mentioned dye image-providing materials, the mordants described in U.S. Pat. Nos. 3,148,061; 3,770,439; 3,709,690; 3,547,649; 3,898,088; and 3,958,995 and Japanese Patent Application (OPI) No. 71,332/'75 are used.

It is preferred that a film-forming acid polymer be used as the neutralizing layer and any acid polymers having film forming ability can be used. Examples of the acid polymers are a monovinyl ester of a copolymer of maleic anhydride and ethylene, a monobutyl ester of a copolymer of maleic anhydride and methyl vinyl ether, a monoethyl ester of maleic anhydride and ethylene, a monopropyl ester of a copolymer of maleic anhydride and ethylene, a monopentyl ester of a copolymer of maleic anhydride and ethylene, a monohexyl ester of a copolymer of maleic anhydride and ethylene, a monoethyl ester of a copolymer of maleic anhydride and methyl vinyl ether, a monopropyl ester of maleic anhydride and methyl vinyl ether, a monobenzyl ester of a copolymer of maleic anhydride and methyl vinyl ether, a monohexyl ester of a copolymer of maleic anhydride and methyl vinyl ether, polyacrylic acid, polymethacrylic acid, copolymers of acrylic acid and methacrylic acid at various ratios, and copolymers of acrylic acid or methacrylic acid and other vinylic monomer (such as an acrylic acid ester, a methacrylic acid ester, a vinyl ether, an acrylamide, a methacrylamide, etc.) at various ratios, preferably containing 50 to 90 mol percent acrylic acid or methacrylic acid. The neutralizing layers utilized in this invention are described in U.S. Pat. Nos. 3,362,819; 3,765,885; and 3,819,371 and French Pat. No. 2,290,699. In particular, the use of polyacrylic acid or a copolymer of acrylic acid and butyl acrylate is preferred.

For the neutralizing timing layer, gelatin, polyvinyl alcohol, polyacrylamide, partially hydrolyzed polyvinyl acetate, a copolymer of β-hydroxyethyl methacrylate and ethyl acrylate, or acetyl cellulose is mainly used. Other materials described in U.S. Pat. Nos. 3,455,686; 3,421,893; 3,785,815; 3,847,615; 4,009,030; and Japanese Patent Application (OPI) No. 14,415/'77 can be used. Furthermore, the above-mentioned neutralizing timing layer may be used together with a polymer layer having large temperature reliance as to the permeation of an alkaline processing solution as described in U.S. Pat. Nos. 4,056,394 and 4,061,496 and Japanese Patent Application Nos. 148,589/'76 (corresponding to U.S. Patent Application Ser. No. 859,636 filed on Dec. 12, 1977) and 144,749/'77 (corresponding to U.S. Patent Application Ser. No. 966,407 filed on Dec. 4, 1978).

EXAMPLE 1

A photosensitive sheet (A) was prepared by coating in succession the following layers on a transparent polyethylene terephthalate support:

(1) A mordant layer containing 3.0 g/m² of the copolymer described in U.S. Pat. No. 3,898,088 having the following repeating unit in the following ratio and 3.0 g/m² of gelatin:

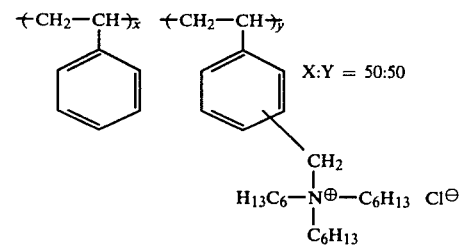

(2) A white reflective layer containing 20 g/m² of titanium oxide and 2.0 g/m² of gelatin.

(3) A light shielding layer containing 2.70 g/m² of carbon black and 2.70 g/m² of gelatin.

(4) A layer containing 0.50 g/m² of the cyan dye image-providing material having the following structure dissolved in 0.10 g/m² of diethyllaurylamide and 0.06 g/m² of tricresyl phosphate, and further 1.14 g/m² of gelatin;

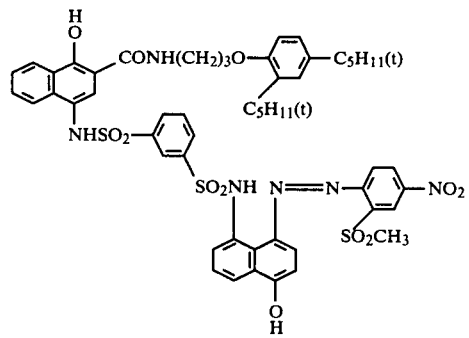

(5) A layer containing a red-sensitive internal latent image-type direct reversal silver iodobromide emulsion (2.5 g/m² as the amount of silver; the halogen composition in the silver halide: 2 mol percent iodine), 2.2 g/m² of gelatin, 0.20 mg/m² of the fogging agent shown by the following formula, and 0.13 g/m² of sodium pentadecylhydroquinonesulfonate;

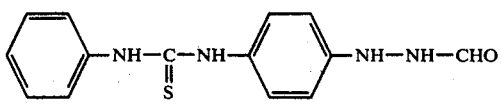

(6) A layer containing 2.6 g/m² of gelatin and 1.0 g/m² of 2,5-dioctylhydroquinone dissolved in 1.6 g/m² of tricresyl phosphate.

(7) A layer containing 0.45 g/m² of a magenta dye image-providing material having the following structure dissolved in 0.10 g/m² of diethyllaurylamide, 0.0074 g/m² of 2,5-di-t-butylhydroquinone, and 0.76 g/m² of gelatin;

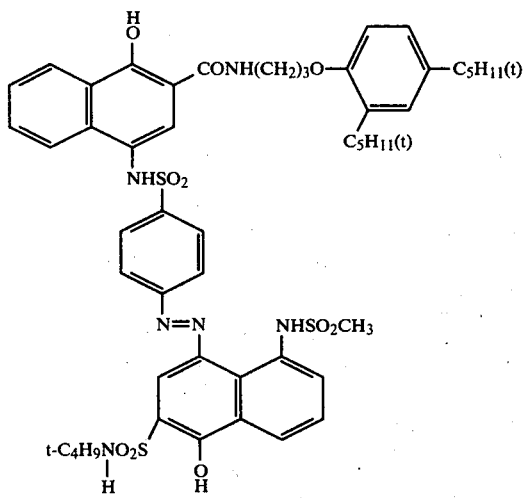

(8) A layer containing a green-sensitive internal latent image-type direct reversal silver iodobromide emulsion (2.1 g/m² of silver; halogen composition of silver iodobromide: 2 mol percent iodine); 1.9 g/m² of gelatin, 0.10 mg/m² of the fogging agent as used in Layer (5), and 0.11 g/m² of sodium pentadecylhydroquinonesulfonate.

(9) A layer containing 2.1 g/m² of gelatin and 0.85 g/m² of 2,5-dioctylhydroquinone dissolved in 1.9 g/m² of tricresyl phosphate.

(10) A layer containing 0.78 g/m² of the yellow dye image-providing material having the following formula dissolved in 0.16 g/m² of diethyllaurylamide, 0.012 g/m² of 2,5-di-t-butylhydroquinone, and 0.78 g/m² of gelatin;

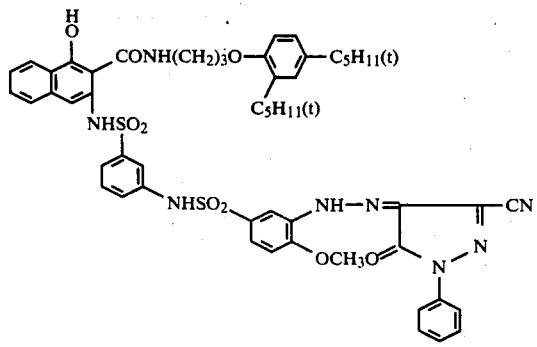

(11) A layer containing a blue-sensitive internal latent image-type direct reversal silver iodobromide emulsion (1.7 g/m² of silver; halogen composition of silver iodobromide: 2 mol percent iodine), 1.6 g/m² of gelatin, 0.09 g/m² of the fogging agent as used in Layer (5) and 0.094 g/m² of sodium pentadecylhydroquinonesulfonate.

(12) A layer containing 0.94 g/m² of gelatin.

Also, a photosensitive sheet (B) was prepared in the same manner as the sheet (A) except that 0.045 g/m² of Compound 1 was further incorporated into Layer (4).

| Processing solution: | |
|---|---|
| 1-Phenyl-4-methyl-4-hydroxymethyl-3-pyrazolidinone | 10 g |
| Methylhydroquinone | 0.18 g |
| 5-Methylbenzotriazole | 4.0 g |
| Sodium Sulfite (anhydrous) | 1.0 g |
| Carboxymethyl Cellulose Sodium Salt | 40.0 g |
| Carbon Black | 150 g |
| Potassium Hydroxide (28% aqueous solution) | 200 ml |
| Water | 550 ml |

The processing solution having the above composition was filled in an amount of 0.8 g in a container which could be ruptured by pressure.

Cover sheet:

A cover sheet (A) was prepared by coating on a polyethylene terephthalate support 15 g/m² of polyacrylic acid (viscosity of about 1,000 c.p. at 25° C. as an aqueous 10% by weight solution) as a neutralizing acid polymer layer and 3.8 g/m² of acetyl cellulose (39.4 g of acetyl group formed by the hydrolysis of 100 g of the acetyl cellulose) and 0.2 g/m² of poly(styrene-co-maleic anhydride) (molar weight: about 10,000; composition ratio: styrene: maleic anhydride=about 1:1) as a neutralizing timing layer.

Processing step:

The cover sheet described above was superposed on the photosensitive sheet (A) or (B) and after exposing to a color test chart from the cover sheet side, the above-described processing solution was spread between the both sheets in a thickness of 85 microns (by the aid of press rollers). The development process was performed at 25° C. and 35° C. After processing, the blue density, green density, and red density of the dye images formed in the image-receiving layer were measured through the transparent support of the photosensitive sheet by means of a Macbeth reflection densitometer one hour after processing, the results are shown in Table 1.

TABLE 1

| | Processing temperature | Blue density | | Green density | | Red density | |
|---|---|---|---|---|---|---|---|
| | | $D_{max}$ | $D_{min}$ | $D_{max}$ | $D_{min}$ | $D_{max}$ | $D_{min}$ |
| Photosensitive sheet (A) (Comparison) | 25° C. | 1.65 | 0.28 | 1.82 | 0.30 | 2.00 | 0.38 |
| Photosensitive sheet (A) (Comparison) | 35° C. | 1.88 | 0.36 | 1.93 | 0.42 | 2.06 | 0.56 |
| Photosensitive sheet (B) (Invention) | 25° C. | 1.64 | 0.26 | 1.73 | 0.27 | 1.90 | 0.34 |
| Photosensitive sheet (B) (Invention) | 35° C. | 1.86 | 0.30 | 1.90 | 0.34 | 2.00 | 0.40 |

From the results shown in the table, it is understood that by incorporating the development inhibitor precursor of this invention in the photosensitive sheet, $D_{min}$ was reduced without lowering $D_{max}$ to much and hence the image quality was improved. This effect was particularly remarkable at the processing temperature of 35°

C. as compared with the comparison case, the addition of the development inhibitor precursor enlarges the allowable range of processing temperatures to the high temperature side.

EXAMPLE 2

A photosensitive sheet (C) was prepared by coating in succession the following layers on a transparent polyethylene terephthalate support;

(1) A mordanting layer the same as in Example 1.

(2) A white reflective layer the same as in Example 1.

(3) A light shielding layer the same as in Example 1.

(4) A layer containing 0.44 g/m² of the cyan DRR compound having the following formula, 0.015 g/m² of 2,5-di-t-butylhydroquinone, 0.11 g/m² of diethyllaurylamide, and 1.1 g/m² of gelatin;

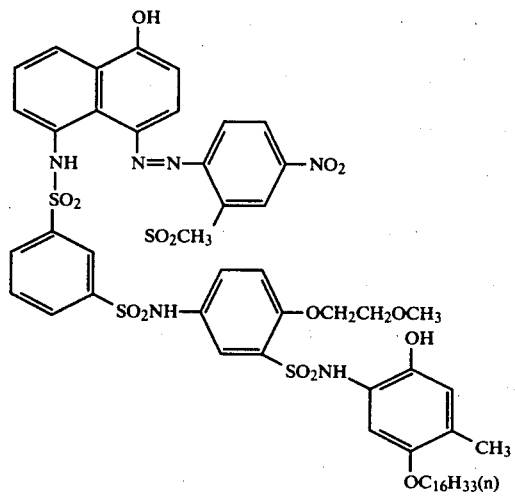

(5) A layer containing a red-sensitive internal latent image-type direct positive silver iodobromide emulsion (the internal latent image-type emulsion prepared by the method described in U.S. Pat. No. 3,761,276; 2.1 g/m² as the silver; halogen composition of silver halide: 2 mol percent iodine), 2.6 g/m² of gelatin, 0.08 mg/m² of the fogging agent having the following formula, and 0.27 g/m² of sodium 5-pentadecyl-hydroquinone-2-sulfonate;

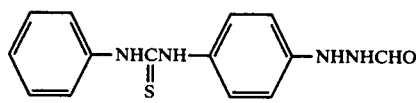

(6) A layer containing 1.9 g/m² of gelatin and 0.85 g/m² of 2,5-di-t-pentadecylhydroquinone.

(7) A layer containing 0.6 g/m² of the magenta DRR compound having the following formula, 0.01 g/m² of 2,5-di-t-butylhydroquinone, 0.13 g/m² of diethyllaurylamide, and 11.1 g/m² of gelatin.

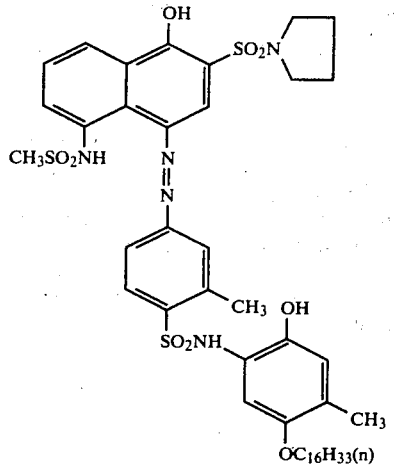

(8) A layer containing a green-sensitive internal latent image type direct positive silver iodobromide emulsion (the internal latent image type emulsion prepared by the method described in U.S. Pat. No. 3,761,276; 1.6 g/m² of silver; halogen composition in the silver halide: 2 mol percent iodine), 1.8 g/m² of gelatin, 0.05 mg/m² of the fogging agent as used in Layer (5), and 0.15 g/m² of sodium 5-pentadecylhydroquinone-2-sulfonate.

(9) A layer containing 1.9 g/m² of gelatin and 1.3 g/m² of 2,5-di-t-pentadecylhydroquinone.

(10) A layer containing 0.91 g/m² of the yellow DRR compound having the following formula, 0.15 g/m² of diethyllaurylamide, 0.012 g/m² of 2,5-di-t-butylhydroquinone, and 0.9 g/m² of gelatin;

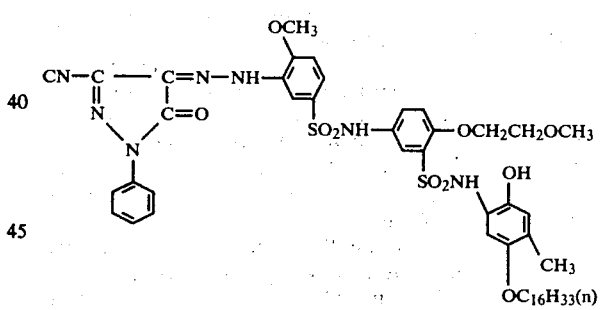

(11) A layer containing a blue-sensitive internal latent image-type direct positive silver iodobromide emulsion (the internal latent image-type emulsion prepared by the method described in U.S. Pat. No. 3,761,276; 2.6 g/m² of silver; halogen composition in the silver halide: 2 mol percent iodine), 2.7 g/m² of gelatin, 0.11 mg/m² of the fogging agent as used in Layer (5), and 0.16 g/m² of sodium 5-pentadecylhydroquinone-2-sulfonate.

(12) A layer containing 1.0 g/m² of gelatin.
Processing solution:
Same as used in Example 1.
Cover sheet:

A cover sheet (B) was prepared by coating in succession the following layers on a polyethylene terephthalate support:

(1) A neutralizing layer containing a copolymer of acrylic acid and butyl acrylate (8:2 by mol ratio) having a weight average molecular weight of 50,000 at a coverage of 22 g/m².

(2) A neutralizing timing layer formed by coating cellulose acetate having an acetylation degree of 52.1% (the amount of acetic acid released by hydrolysis of the cellulose acetate was 0.521 g per gram of the sample) and a copolymer of styrene and maleic anhydride (1:1 by mol ratio) having a weight average molecular weight of about 10,000 at a ratio of 95 to 5 at coverages of 3 g/m².

(3) A layer formed by coating a polymer latex prepared by emulsion polymerizing styrene, butyl acrylate, and acrylic acid at a ratio of 52:42:6 by weight ratio at a coverage of 3 g/m² as solid.

Also, a cover sheet (C) and a cover sheet (D) were prepared as in the cae of preparing the cover sheet (B) as follows:

Cover sheet (C):

Cover sheet (C) was prepared in the same manner as the cover sheet (B) except that 0.3 m.mol/m² (0.073 g/m²) of Compound 1 was incorporated in the timing layer, Layer (2).

Cover sheet (D):

Cover sheet (D) was prepared in the same manner as the cover sheet (B) except that 0.3 m.mol/m² (0.069 g/m²) of 5-(2-cyanoethylthio)-1-phenyltetrazole described in U.S. Pat. No. 4,009,029 as a comparison was incorporated in the timing layer, Layer (2).

Processing step:

The cover sheet (B), (C) or (D) was superposed on the above-mentioned photosensitive sheet (C) and after image-wise exposing through a continuous gradation wedge from the cover sheet side, the above-described processing solution was spread between the both sheets at a thickness of 80 microns (by the aid of press rollers). The processing was performed at 15° C., 25° C. and 35° C. Thereafter, the color positive image obtained in each sheet was measured and the photographic properties of the color images are shown in Table 2.

TABLE 2

| | Processing temperature | Blue density | | Green density | | Red density | |
|---|---|---|---|---|---|---|---|
| | | $D_{max}$ | $D_{min}$ | $D_{max}$ | $D_{min}$ | $D_{max}$ | $D_{min}$ |
| Cover sheet (B) (Comparison) | 15° C. | 1.66 | 0.25 | 1.83 | 0.28 | 1.88 | 0.34 |
| Cover sheet (B) (Comparison) | 25° C. | 1.77 | 0.28 | 1.92 | 0.31 | 1.98 | 0.35 |
| Cover sheet (B) (Comparison) | 35° C. | 1.83 | 0.32 | 1.95 | 0.35 | 1.95 | 0.43 |
| Cover sheet (C) (This Invention) | 15° C. | 1.68 | 0.24 | 1.80 | 0.26 | 1.90 | 0.33 |
| Cover sheet (C) (This Invention) | 25° C. | 1.78 | 0.26 | 1.91 | 0.28 | 1.97 | 0.32 |
| Cover Sheet (C) (This Invention) | 35° C. | 1.80 | 0.28 | 1.92 | 0.30 | 1.95 | 0.38 |
| Cover sheet (D) (Comparison) | 15° C. | 1.65 | 0.24 | 1.80 | 0.27 | 1.86 | 0.33 |
| Cover sheet (D) (Comparison) | 25° C. | 1.76 | 0.26 | 1.93 | 0.29 | 1.95 | 0.32 |
| Cover sheet (D) (Comparison) | 35° C. | 1.78 | 0.30 | 1.91 | 0.31 | 1.96 | 0.39 |

As is shown in Table 2, in the cover sheet (C) containing Compound 1 of this invention, the increase of $D_{min}$ at 35° C. was prevented as compared with the case of using the cover sheet (B), meaning that while even if there were some variation about $D_{max}$, they did not have much effect on the image quality, the slight reduction in $D_{min}$ improved remarkably the image quality, the cover sheet of this invention enlarged the allowable range of the processing temperature not only at a low temperature side but also at a high temperature side, and showed excellent properties as compared with the comparison cover sheet (D).

EXAMPLE 3

Photosensitive sheet

The photosensitive sheet (C) in Example 2 was used.

Cover sheet

A cover sheet (E) was prepared by coating in succession the following layers on a polyethylene terephthalate support:

(1) A neutralizing layer formed by adding 1.8 m.mol/m² (0.44 g/m²) of Compound 1 to the neutralizing layer (1) of the cover sheet (B) in Example 2.

(2) Same as Layer (2) of the cover sheet (B) in Example 2.

(3) Same as Layer (3) of the cover sheet (B) in Example 2.

A cover sheet (F) was also prepared in the same manner as cover sheet (E) except that 1.8 m.mol/m² (0.42 g/m²) of 5-(2-cyanoethylthio)-1-phenyltetrazole was added to the neutralizing layer (1) of the cover sheet (E) as a comparison compound in place of Compound 1.

Processing solution

The processing solution used in Example 1.

Processing step

The cover sheet (E) or (F) prepared above was superposed on the above-mentioned photosensitive sheet (C) and proposed as in Example 2. The processing was performed at 25° C. Good color images were obtained in each cover sheet.

As a control test, the cover sheet (B) of Example 2 was processed in the same manner as above.

Fading test

After allowing the film units thus processed to stand for one day, the densities of the color images were measured and the film units were allowed to stand for 4 days in a closed container at 80° C. in the presence of silica gel. Thereafter, the densities of the color images were measured again and the reduction percentage in density with respect to the control (over sheet (B)) at the point where the initial density was 1.5 by a reflection density was measured, the results being shown in Table 3.

TABLE 3

| | Blue density | Green density |
|---|---|---|
| Cover sheet (E) (Invention) | 0.7% | 4.6% |
| Cover sheet (F) (Comparison) | 0.8% | 20% |

Wherein, the reduction percentage is defined as follows:

$$\text{Reduction percentage} = \frac{(I) - (II)}{1.5} \times 100 \ (\%)$$

(I): The density of the control unit having initial density of 1.5 after fading.
(II): The density of the sample unit of initial density of 1.5 after fading.

As is shown in Table 3, the use of the development inhibitor precursor of this invention showed less fading in the green density as compared with the comparison precursor and gave unexpectedly excellent properties.

EXAMPLE 4

A mixture of 7.78 g of the yellow dye-forming coupler having the following structure, B 0.325 g of Compound 1, 2.5 ml of dibutyl phthalate, 35 ml of ethyl acetate, and 0.4 g of α-sulfosuccinic acid dioctyl ester sodium salt was refluxed and the solution formed was poured in 120 ml of an aqueous solution containing 10 g of gelatin, 0.1 g of succinic acid, and 0.05 g of sodium hydrogensulfite and finely dispersed therein by stirring vigorously for 19 minutes using a homogenizer.

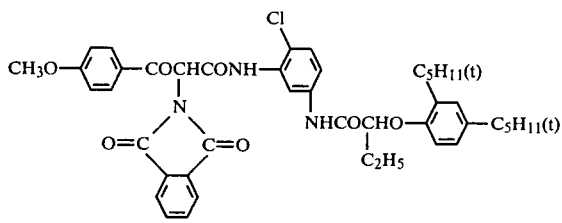

The whole amount of the dispersion was mixed with 200 g of a blue-sensitive silver halide emulsion containing 53 milli mols of a silver halide (halogen composition: 2 mol percent iodine, 83 mol percent bromine and 15 mol percent chlorine) having a mean grain size of 0.6 micron, 12 g of gelatin, and 30 ml of 5-methyl-6-hydroxy-1,3,4-triazaindrizine and after adding thereto 5 ml of an aqueous solution of 4 percent 2-hydroxy-4,6-dichloro-s-triazine.sodium salt as a hardening agent and 2 ml of an aqueous solution of 5% dodecyl sulfate sodium salt as a coating aid, the mixture was coated on a polyethylene-coated paper at a dry thickness of 2.5 microns. The blue-sensitive silver halide emulsion layer thus formed contained 720 mg/m$^2$ (0.93 m.mol/m$^2$) of the coupler, 30 mg/m$^2$ of Compound 1, and 4.9 m.mol/m$^2$ of the silver halide.

Then, an interlayer composed of 35 mg/m$^2$ of 2,5-di-tert-octylhydroquinone, 50 mg/m$^2$ of dibutyl phthalate, and 2 g/m$^2$ of gelatin was coated as a 2nd layer on the blue-sensitive emulsion layer.

Then, a green-sensitive silver halide emulsion containing 695 mg/m$^2$ of 1-(2',4',6'-trichlorophenyl)-3-{3''-[α-(2''',4'''-tert-amylphenoxy)butylamido]benzamido}-5-pyrazolone, 45 mg/m$^2$ of 2,5-di-tert-octylhydroquinone, 70 mg/m$^2$ of 6,6'-dihydroxy-4,4,4',4',7,7'-hexamethyl-bis-2,2'-spirochroman, and 1.5 g/m$^2$ of tri-n-hexyl phosphate was coated thereon as a 3rd layer at a thickness of 4 microns.

A mixture of 4.92 g of 2-benzotriazole-4-tert-butylphenol, 2.46 g of 2-(5'-chlorobenzotriazolyl)-4-methyl-6-tert-butylphenol, 0.246 g of 2,5-di-tert-octylhydroquinone, 0.31 g of Compound 1, 12.3 g of dibutyl phthalate, and 25 ml of ethyl acetate was refluxed under heating and the solution formed was poured in 120 ml of an aqueous solution containing 10 g of gelatin, 0.1 g of succinic acid, 0.05 g of sodium hydrogensulfite, and 0.5 g of sodium p-dodecylbenzenesulfonate and finely dispersed therein by stirring vigorously for 10 minutes using a homogenizer. And after adding thereto an aqueous solution containing 20 g of gelatin, the mixture was coated thereon as a 4th layer. The layer contained 0.4 g/m$^2$ of 2-benzotriazole-4-tert-butylphenol, 0.2 g/m$^2$ of 2-(5'-chlorobenzotriazolyl-4-methyl-6-tert-butylphenol, 20 mg/m$^2$ of 2,5-di-tert-octylhydroquinone, 25 mg/m$^2$ of the precursor (Compound 1), 1 g/m$^2$ of dibutyl phthalate, and 2.5 g/m$^2$ of gelatin.

Then, a red-sensitive silver halide emulsion layer containing 520 mg/m$^2$ of 2,4-dichloro-5-methyl-6-{α-(2',4'-di-tert-amylphenoxy)butylamide}phenol and 1.5 g/m$^2$ of dibutyl phthalate was coated thereon as a 5th layer at a thickness of 2.5 microns.

Thereafter, gelatin was coated as a protective layer at a thickness of 1.5 microns to provide a color photographic paper, which is called "photosensitive material IV-1".

Also, color photographic paper IV-2 was prepared in the same manner as above except that the development inhibitor precursor (Compound 1) was not used in the 1st layer and the 4th layer.

After subjecting these photosensitive materials to stepwise sensitometeric exposure by blue light, green light, and red light, they were processed as follows:

| Processing step | Temperature | Time |
| --- | --- | --- |
| 1. Color development | 32° C. | 3 min. |
| 2. Blix | 32° C. | 3 min. |
| 3. Wash | 20° C. | 4 min. |

The compositions of the color developer and the blix solution used in the above steps were as follows:

| Color developer: | |
| --- | --- |
| Benzyl Alcohol | 12 g |
| Sodium Hexametaphosphate | 2 g |
| Anhydrous Sodium Sulfite | 2 g |
| Sodium Carbonate (mono-hydrate) | 27.5 g |
| Hydroxyamine Sulfate | 2.5 g |
| 4-Amino-3-methyl-N-(β-methanesulfonamidoethyl)-N-ethylaniline sesquisulfate | 4 g |
| Water to make | 1 liter. |

| Blix solution: | |
| --- | --- |
| Ammonium Thiosulfate | 105 g |
| Sodium Sulfite | 80 g |
| EDTA (2-sodium salt) | 35 g |
| Ferrous Chloride (6-hydrate) | 25 g |
| Potassium Thiocyanate | 10 g |
| Water to make | 1 liter. |

The optical reflection density of the colored portions of the sample obtained after the processing was measured using complementary color, the results being shown in Table 4.

TABLE 4

| Sample | Precursor | Color | Fog density | Max density | Relative sensitivity |
| --- | --- | --- | --- | --- | --- |
| IV-1 | Compound 1 | Yellow (Blue density) | 0.07 | 2.40 | 90 |
| | | Magenta (Green density) | 0.07 | 2.60 | 100 |
| | | Cyan (Red density) | 0.08 | 2.75 | 100 |
| IV-2 | none | Yellow (Blue density) | 0.15 | 2.50 | 100 |
| | | Magenta (Green density) | 0.12 | 2.70 | 100 |
| | | Cyan (Red density) | 0.10 | 2.80 | 100 |

As is clear from Table 4, the photographic paper of this invention had substantially the same maximum density and relative sensitivity as those of the comparison sample and was able to provide a beautiful white background having greatly reduced fog density.

Preferred embodiments of this invention are as follows:

1. A photographic element comprising a support having thereon at least one silver halide emulsion layer associated with a development inhibitor precursor represented by the formula (I)

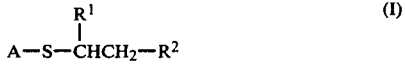

wherein A represents a phenyl group, a substituted phenyl group, or a 5- or 6-membered nitrogen-containing heterocyclic ring; said A splitting together with the sulfur atom of the above molecule from the residue of the molecule to provide a silver halide development inhibitor; $R^1$ represents an alkyl group of 1 to 4 carbon atoms; and $R^2$ represents a cyano group, a carbamoyl group or the group

wherein $R^3$ represents an aryl group.

2. The photographic element of the preferred embodiment 1 wherein $R^2$ is a cyano group.

3. The photographic element of the preferred embodiment 1 wherein A is a tetrazole ring or a phenyltetrazole ring and $R^2$ is a cyano group.

4. The photographic element of the preferred embodiment 1 wherein the development inhibitor precursor is 5-(2-cyano-1-methylethylthio)-1-phenyltetrazole.

5. The photographic element of the preferred embodiment 1 wherein said photographic element is a photographic element for color diffusion transfer process further comprising a dye image-providing material associated with said silver halide emulsion layer, an image-receiving element, an alkaline processing composition, and a neutralizing mechanism for neutralizing said alkaline processing composition.

6. The photographic element of the preferred embodiment 1 wherein said photographic element is a photographic element for color diffusion transfer process including a photosensitive sheet comprising an image-receiving element having on a transparent support an image-receiving layer for fixing diffusible dyes therein, a white reflective layer, a light shielding layer, and a photosensitive element comprising at least one silver halide emulsion layer and a dye image-providing material associated with the silver halide emulsion layer; and an alkaline processing composition for developing said exposed photosensitive element; and a cover sheet comprising a separate support a neutralizing mechanism for neutralizing said alkaline processing composition.

7. The photographic element of the preferred embodiment 6 wherein the development inhibitor precursor of the general formula is contained in said cover sheet.

8. The photographic element of the preferred embodiment 6 wherein the development inhibitor precursor is 5-(2-cyano-1-methylethylthio)-1-phenyltetrazole.

9. The photographic element of the preferred embodiment 6 wherein the silver halide emulsion is an internal latent image-type direct positive silver halide emulsion.

10. The photographic element of the preferred embodiment 9 wherein the dye image-providing material associated with the internal latent image type direct positive silver halide emulsion is a DRR compound.

11. The photographic element of the preferred embodiment 1, wherein said development inhibitor precursor is represented by the formula (II)

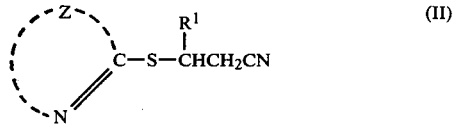

wherein Z represents the non-metallic atomic group necessary to complete a 5- or 6-membered heterocyclic ring which may be substituted or condensed with another ring, said heterocyclic rings being capable of splitting together with the sulfur atom of the molecule to provide a silver halide development inhibitor and $R^1$ represents an alkyl group having 1 to 4 carbon atoms.

12. The photographic element of the preferred embodiment 11, wherein said heterocyclic ring is a tetrazole ring, a phenyl tetrazole ring, a 1,2,4-triazole ring, benzoxazole ring, a benzothiazole ring, a pyridine ring or a pyrimidine ring.

13. The photographic element of the preferred embodiment 1, wherein said development inhibitor precursor is present in an amount of about $10^{-4}$ mol to $5 \times 10^{-2}$ moles per mol of silver halide in the associated silver halide emulsion layer.

14. The photographic element of the preferred embodiments 5 or 6, wherein said development inhibitor precursor is incorporated into an image-receiving layer.

15. The photographic element of the preferred embodiments 5 or 6, wherein said development inhibitor precursor is incorporated into a silver halide emulsion layer or a hydrophilic colloid layer adjacent a silver halide emulsion layer.

16. The photographic element of the preferred embodiments 5 or 6, wherein said development inhibitor precursor is incorporated into a layer containing a dye image-providing material.

17. The photographic element of the preferred embodiment 6, wherein said development inhibitor precursor is incorporated into said light reflective layer.

18. The photographic element of the preferred embodiment 7, wherein said development inhibitor precursor is incorporated in a neutralizing layer.

19. The photographic element of the preferred embodiment 7, wherein said development inhibitor precursor is incorporated in a neutralizing timing layer.

20. A method of inhibiting development which comprises developing a silver halide emulsion layer in the presence of a development inhibit precursor represented by the formula (I)

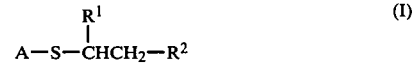

wherein A represents a phenyl group, a substituted phenyl group, or a 5- or 6-membered nitrogen-containing heterocyclic ring; $R^1$ represents an alkyl group of 1 to 4 carbon atoms and $R^2$ represents a cyano group, a carbamoyl group, or the group —COR$^3$ wherein R$^3$ represents an aryl group such that upon contact with said developer, A splits together with the sulfur atom in the above molecule from the residue of the molecule to inhibit silver halide development.

While the invention has been described in detail and with reference to specific embodiments thereof, it will be apparent to one skilled in the art that various changes and modifications can be made without departing from the spirit and scope thereof.

What is claimed is:

1. A photographic element for the color diffusion transfer process comprising a support having thereon at least one silver halide emulsion layer associated with a development inhibitor precursor represented by the formula

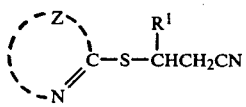

wherein Z represents the non-metallic atomic group necessary to complete a 5- or 6-membered heterocyclic ring which may be substituted or condensed with another ring, said heterocyclic rings being capable of splitting together with the sulfur atom of the molecule to provide a silver halide development inhibitor and R$^1$ represents an alkyl group having 1 to 4 carbon atoms, a dye-image providing material associated with said silver halide emulsion layer, an image-receiving element, an alkaline processing composition, and a neutralizing mechanism for neutralizing said alkaline processing composition.

2. The photographic element of claim 1, wherein said photographic element includes a photosensitive sheet comprising an image-receiving element having on a transparent support an image-receiving layer for fixing diffusible dyes therein, a light reflective layer, a light shielding layer, and a photosensitive element comprising at least one silver halide emulsion layer and a dye image-providing material associated with the silver halide emulsion layer; an alkaline processing composition for developing said photosensitive element after exposure; and a cover sheet comprising a separate support; and a neutralizing mechanism for neutralizing said alkaline processing composition.

3. The photographic element of claim 2, wherein the development inhibitor precursor is contained in said cover sheet.

4. The photographic element of claim 2, wherein the development inhibitor precursor is 5-(2-cyano-1-methylethylthio)-1-phenyltetrazole.

5. The photographic element of claim 2, wherein the silver halide emulsion is an internal latent image-type direct positive silver halide emulsion.

6. The photographic element of claim 5, wherein the dye image-providing material associated with the internal latent image type direct positive silver halide emulsion is a DDR compound.

7. The photographic element of claim 1, wherein said development inhibitor precursor is present in an amount of about $10^{-4}$ mol to $5 \times 10^{-2}$ moles per mol of silver halide in the associated silver halide emulsion layer.

8. The photographic element of claim 1, wherein said development inhibitor precursor is incorporated into an image-receiving layer.

9. The photographic element of claim 1, wherein said development inhibitor precursor is incorporated into a silver halide emulsion layer or a hydrophilic colloid layer adjacent a silver halide emulsion layer.

10. The photographic element of claim 1, wherein said development inhibitor precursor is incorporated into a layer containing a dye image-providing material.

11. The photographic element of claim 2, wherein said development inhibitor precursor is incorporated into said light reflective layer.

12. The photographic element of claim 3, wherein said development inhibitor precursor is incorporated in a neutralizing layer.

13. The photographic element of claim 3, wherein said development inhibitor precursor is incorporated in a neutralizing timing layer.

14. A photographic element comprising a support having thereon at least one silver halide emulsion layer which is associated with a dye image-providing material and which is associated with a development inhibitor precursor represented by the formula

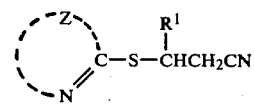

wherein Z represents the non-metallic atomic group necessary to complete a 5- or 6-membered heterocyclic ring which may be substituted or condensed with another ring, said heterocyclic rings being capable of splitting together with the sulfur atom of the molecule to provide a silver halide development inhibitor and R$^1$ represents an alkyl group having 1 to 4 carbon atoms.

15. The photographic element of claim 1, wherein said heterocyclic ring is a tetrazole ring or a phenyltetrazole ring.

16. The photographic element of claim 14, wherein the development inhibitor precursor is 5-(2-cyano-1-methylethylthio)-1-phenyltetrazole.

* * * * *